(12) United States Patent
Cawse (10) Patent No.: US 6,728,641 B1
(45) Date of Patent: Apr. 27, 2004

(54) METHOD AND SYSTEM FOR SELECTING A BEST CASE SET OF FACTORS FOR A CHEMICAL REACTION

(75) Inventor: James Norman Cawse, Pittsfield, MA (US)

(73) Assignee: General Electric Company, Schenectady, NY (US)

( * ) Notice: Subject to any disclaimer, the term of this patent is extended or adjusted under 35 U.S.C. 154(b) by 12 days.

(21) Appl. No.: 09/692,343

(22) Filed: Oct. 20, 2000

Related U.S. Application Data (60) Provisional application No. 60/177,325, filed on Jan. 21, 2000.

(51) Int. Cl.[7] .................... G01N 33/48; G01N 33/566; C12Q 1/00; B01J 31/00; B01J 37/00
(52) U.S. Cl. ........................ 702/19; 435/4; 436/501; 502/104
(58) Field of Search ................. 702/19; 435/4; 436/501; 502/104

(56) References Cited

U.S. PATENT DOCUMENTS

| | | |
|---|---|---|
| 5,143,854 A | 9/1992 | Pirrung et al. |
| 5,542,043 A | 7/1996 | Cohen et al. |
| 5,901,069 A | 5/1999 | Agrafiotis et al. |
| 5,917,077 A | 6/1999 | Chaudhari et al. |
| 6,044,212 A | 3/2000 | Flavin et al. |

FOREIGN PATENT DOCUMENTS

| | | |
|---|---|---|
| WO | 0023921 | 4/2000 |

OTHER PUBLICATIONS

Xiang, X–D, "Combinatiorial Materials Synthesis and High–throughput Screening: An Integrated Materials Chip Approach to Mapping Phase Diagrams and Discovery and Optimization of Functional Materials". Biotechnology and Bioengining, vol. 61, No. 4, 1998/1999.*

Wolf et al., "An Evolutionary Approach in the Combinatorial Selection and Optimization of Catalytic Materials", Applied Catalysis A: General 200, 63–77 (2000).

J.M. Newsam: "Design of Catalysts and Catalyst Libraries Computational Techniques in High Throughput Experimentation for catalysis", NATO ASI Series. Series C: Mathematical and Physical Sciences, 1999, pp. 301–335.

D. Wolf et al.: "An Evolutionary Approach in the Combinatorial Selection and Optimization of Catalytic Materials", Applied Catalysis A: General, vol. 200, No. 1–2, Aug. 28, 2000, pp. 63–77.

H. Okamoto et al: "Design of a Robotic Workstation for Automated Organic Synthesis", Laboratory Robotics and Automation, vol. 12, 2000, pp. 2–11.

Hau Du et al.,: "An Automated Microscale Chemistry Workstatin Capable of Parallel, Adaptive Experimentation", Chemometrics and Intelligen Laboratory Systems, vol. 48, No. 2, Aug. 2, 1999, pp. 181–203.

H. Van de Waterbeemd et al.: "Glossary of Terms used in Computational Drug Design", Compendium of Chemical Terminology, International Union of Pure & Applied Chemistry (IUPAC) Recommendations, Oxford, Blackwell Scientific, 1987, pp. 1137–1152.

P. Y. Kuo et al.: "A Planning Module for Performing Grid Search, Factorial Design, and Related Combinatorial Studies on an Automated Chemistry Workstation", Chemometrics and Intelligent Laboratory Systems, vol. 48, No. 2, Aug. 2, 1999, pp. 219–234.

A. Beutelspacher, in The CRC Handbook of Combinatorial Designs, C. J. Colbourn and J. H. Dinitz, eds, CRD Press, New York, 1996, pp. 119 and 694.

D. M. Cohen, et al., The AETG System: An Approach to Testing Based on Combinatorial Design, IEEE Transactions on Software Engineering, vol. 23, No. 7, Jul. 1997.

* cited by examiner

Primary Examiner—John S. Brusca
Assistant Examiner—Shubo (Joe) Zhou
(74) Attorney, Agent, or Firm—Philip D. Freedman; Andrew J. Caruso (57) ABSTRACT

A method selects a best case set of factors of a chemical reaction by defining a chemical experimental space by (i) identifying relationships between factors of a candidate chemical reaction space; and (ii) determining a chemical experimental space comprising a table of test cases for each of the factors based on the identified relationships between the factors with the identified relationships based on researcher specified n-tuple combinations between identities of the relationships. A combinatorial high throughput screening (CHTS) method is effected on the chemical experimental space to select the best case set of factors. A system for selecting a best case set of factors of a chemical reaction, comprises a processor, reactor and an evaluator. The processor defines a chemical experimental space by (i) identifying relationships between factors of a candidate chemical reaction space; and (ii) determining the chemical experimental space comprising a table of test cases for each of the factors based on the identified relationships between the factors with the identified relationships based on researcher specified n-tuple combinations between identities of the relationships. The reactor and evaluator select a best case set of factors from the chemical experimental space by a combinatorial high throughput screening (CHTS) method to select a best case set of factors.

41 Claims, 6 Drawing Sheets

FIG. 1

Possible Combinations for Six Factors

- ◆ 2 Way
- ■ 3 Way
- × 5 Way
- ✱ 6 Way

FIG. 2

A highly active ternary catalyst bounded by low activity binaries

| | $f_1$ | $f_2$ | $f_3$ | $f_4$ |
|---|---|---|---|---|
| 30 | $v_1$ | $v_1'$ | $v_1''$ | $v_1'''$ |
| | $v_2$ | $v_2'$ | $v_2''$ | $v_2'''$ |
| | $v_3$ | $v_3'$ | $v_3''$ | $v_3'''$ |

| $(\alpha_1, \alpha_2)$ | $a_1, \lambda=0$ | $a_2, \lambda=1$ | $a_3, \lambda=2$ | $a_4$ |
|---|---|---|---|---|
| (0,0) | 0 | 0 | 0 | 0 |
| (1,0) | 1 | 1 | 1 | 0 |
| (2,0) | 2 | 2 | 2 | 0 |
| (0,1) | 0 | 1 | 2 | 1 |
| (1,1) | 1 | 2 | 0 | 1 |
| (2,1) | 2 | 0 | 1 | 1 |
| (0,2) | 0 | 2 | 1 | 2 |
| (1,2) | 1 | 0 | 2 | 2 |
| (2,2) | 2 | 1 | 0 | 2 |

| $f_1$ | $f_2$ | $f_3$ | $f_4$ | $f_5$ | $f_6$ | $f_7$ | $f_8$ | $f_9$ |
|---|---|---|---|---|---|---|---|---|
| 0 OR 1 | 0 OR 1 | 0 OR 1 | 0 OR 1 | 0 OR 1 | 0 OR 1 | 0 OR 1 | 0 OR 1 | 0 OR 1 |

44

| $f_1$ | $f_2$ | $f_3$ |
|---|---|---|
| 0 OR 1 | 0 OR 1 | 0 OR 1 |

45

| 0 | 0 | 0 |
|---|---|---|
| 0 | 1 | 1 |
| 1 | 0 | 1 |
| 1 | 1 | 0 |

46

| 0 | 0 | 0 | 0 | 0 | 0 | 0 | 0 | 0 |
|---|---|---|---|---|---|---|---|---|
| 0 | 0 | 0 | 1 | 1 | 1 | 1 | 1 | 1 |
| 1 | 1 | 1 | 0 | 0 | 0 | 1 | 1 | 1 |
| 1 | 1 | 1 | 1 | 1 | 1 | 0 | 0 | 0 |
| 0 | 0 | 0 | 0 | 0 | 0 | 0 | 0 | 0 |
| 0 | 1 | 1 | 0 | 1 | 1 | 0 | 1 | 1 |
| 1 | 0 | 1 | 1 | 0 | 1 | 1 | 0 | 1 |
| 1 | 1 | 0 | 1 | 1 | 0 | 1 | 1 | 0 |

FIG. 6

METHOD AND SYSTEM FOR SELECTING A BEST CASE SET OF FACTORS FOR A CHEMICAL REACTION

This application claims the priority of Provisional Application Ser. No. 60/177,325, filed Jan. 21, 2000.

BACKGROUND OF THE INVENTION

The present invention relates to a method and system for selecting best case set of factors for a chemical reaction. Particularly, the invention is directed to a method and system for defining an experimental space and conducting a combinatorial high throughput screening (CHTS) of the experimental space to determine a best case set of reaction factors.

In experimental reaction systems, each potential combination of reactant, catalyst and condition must be evaluated in a manner that provides correlation to performance in a production scale reactor. Combinatorial organic synthesis (COS) is a high throughput screening (HTS) methodology that was developed for pharmaceuticals. COS uses systematic and repetitive synthesis to produce diverse molecular entities formed from sets of chemical "building blocks." As with traditional research, COS relies on experimental synthesis methodology. However instead of synthesizing a single compound, COS exploits automation and miniaturization to produce large libraries of compounds through successive stages, each of which produces a chemical modification of an existing molecule of a preceding stage. A library is a physical, trackable collection of samples resulting from a definable set of processes or reaction steps. The libraries comprise compounds that can be screened for various activities.

The technique used to prepare such libraries involves a stepwise or sequential coupling of building blocks to form the compounds of interest. For example, Pirrung el al., U.S. Pat. No. 5,143,854 discloses a technique for generating arrays of peptides and other molecules using, for example, light-directed, spatially-addressable synthesis techniques. Pirrung et al. synthesizes polypeptide arrays on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of desired lengths and sequences are synthesized.

The methodology of COS has been slow in application to screening to develop chemical production scale reactions because of the difficulty in emulating such reactions on the combinatorial micro-scale. For example, catalyst testing is typically accomplished in bench scale or larger pilot plants by contacting a feed to a continuous flow reactor with a catalyst under near steady state reaction conditions. Rapid combinatorial screening of reactants, catalysts, and associated process conditions requires that a large number of reaction and/or catalytic systems be tested simultaneously. The large number of systems are parameters that can define a very large, multidimensional experimental space.

Figure 1:
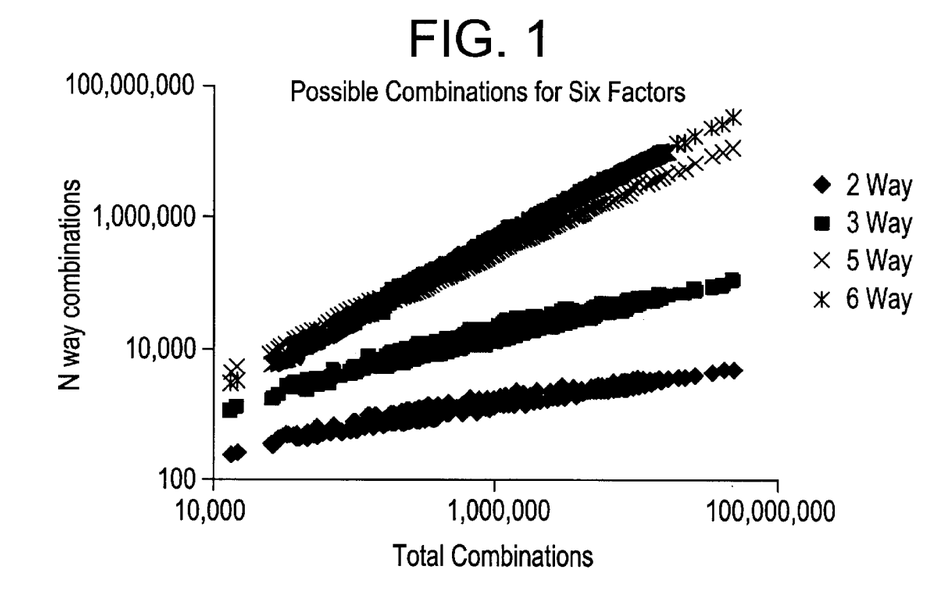
FIG. 1 is a graph of six factor combinations.

For example, even a simple commercial process may have five or six critical factors, each of which can have 2 to 20 levels. These factors can include reactants, catalysts and processing conditions. As shown in FIG. 1, the number of possible combinations of factors can become very large, depending on the number of levels. In addition, little may be known about the reaction kinetics and the role of a catalyst. Accordingly, it may be necessary to search hundreds or thousands of combinations to find a handful of "leads" (i.e., combinations that may lead to commercially valuable applications).

Figure 2:
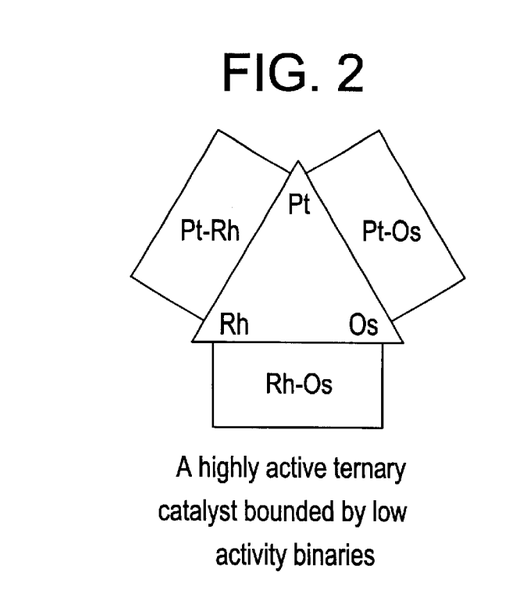
FIG. 2 is a schematic representation of a ternary catalyst bounded by low activity binaries.

T. E. Mallouk et al. in Science, 1998, 1735 showed that effective ternary combinations can exist in a system in which none of the binary combinations are effective. As shown in FIG. 2, investigating binary combinations alone can result in completely ineffective exploration of an experimental space. However, as seen in FIG. 1, the number of tertiary, 4-way, 5-way, and 6-way combinations rapidly becomes extremely large. It is extremely difficult to examine all possibilities of such a complex space even with a very productive high throughput screening (HTS) system. There is a need for improved methods for rapidly, yet effectively investigating a complex experimental space relating to these process combinations.

BRIEF SUMMARY OF THE INVENTION

Accordingly, the invention is directed to a method and system for sampling an experimental space for combinatorial high throughput screening (CHTS). CHTS is an HTS methodology that incorporates characteristics of COS. The definition of the experimental space permits a CHTS investigation of highly complex systems. The method selects a best case set of factors of a chemical reaction. The method comprises defining a chemical experimental space by (i) identifying relationships between factors of a candidate chemical reaction space; and (ii) determining a chemical experimental space comprising a table of test cases for each of the factors based on the identified relationships between the factors with the identified relationships based on researcher specified n-tuple combinations between identities of the relationships. A CHTS method is effected on the chemical experimental space to select a best case set of factors.

In another embodiment, a system for selecting a best case set of factors of a chemical reaction, comprises a processor, reactor and an evaluator. The processor defines a chemical experimental space by (i) identifying relationships between factors of a candidate chemical reaction space and (ii) determining the chemical experimental space comprising a table of test cases for each of the factors based on the identified relationships between the factors with the identified relationships based on researcher specified n-tuple combinations between identities of the relationships. The reactor and evaluator select a best case set of factors from the chemical experimental space by a CHTS method to select a best case set of factors.

DETAILED DESCRIPTION OF THE INVENTION

According to the invention, an algorithm can be applied to determine a minimal number of experimental runs necessary to effectively explore an experimental space by CHTS. The algorithm can be embodied in a computer software program. The software program can be maintained on a server for use by end researchers over a network.

In a preferred embodiment, a researcher provides factors that may impact the reaction or process of interest as well as identities for those factors. In this context, the term "factors" can include reactants, solvents, carriers, catalysts and chemically inert substances that are present to affect a physical property of one or more components of the reactant system. In various embodiments, the term "factor" can further include reaction or process conditions, such as temperature, flow rate, pressure, or reaction atmosphere. The term "identity" refers to a factor's value or makeup—whether in kind or amount. The use of a metric "identity" will necessarily vary depending on a given factor. For example, identity of a reactant may refer to chemical identity or concentration, while identity of a factor such as pressure will be a value or ratio.

The researcher can then provide instructions regarding whether given factors interact with each other. The algorithm then determines a minimal number of necessary experimental runs embodied in a table. In this application, a table is a list of relationships between fields (factors) generated by deterministic procedures as hereinafter described. The factors of one table can be merged with other tables to produce a single table. The merged table is used as a template for parallel chemical reactions and/or high-throughput screening to determine the efficacy of the various combinations of factor identities in the reaction or process of interest.

An example of an acceptable software program for determining the minimal number of experimental runs is the AETG$^{SM}$ System available from Telcordia™ Technologies, Inc., Morristown, N.J. The AETG™ System is and has always been lauded and marketed as a software development program and has heretofore not been utilized as part of a combinatorial chemistry effort.

These and other features will become apparent from the drawings and following detailed discussion, which by way of example without limitation describe preferred embodiments of the present invention.

Figure 3:
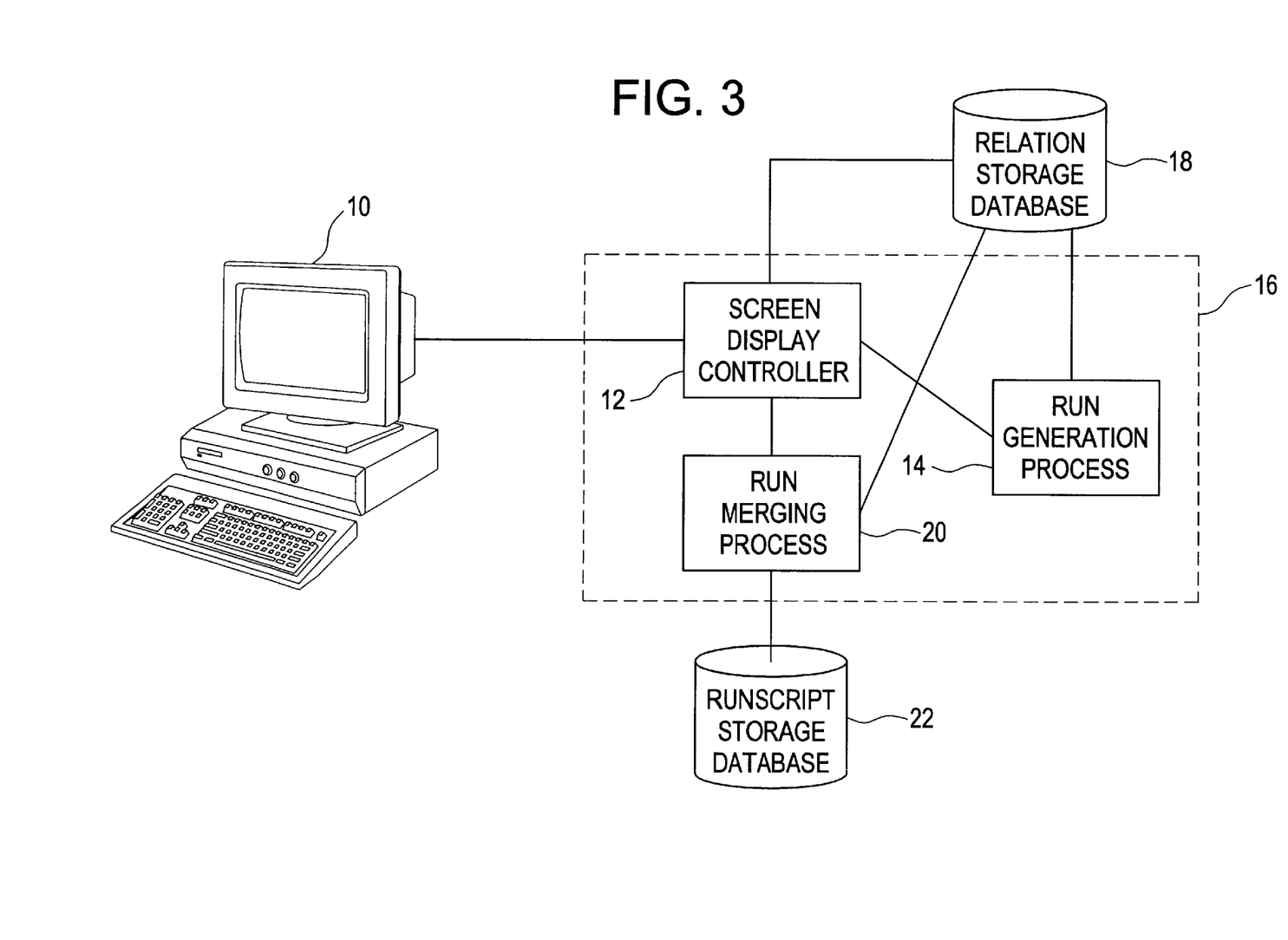
FIG. 3 is a schematic representation of a method and system for defining an experimental space for CHTS.

An illustrative embodiment of the present method is shown in FIG. 3, which includes a terminal 10. A researcher enters identities for factors into the terminal 10 (a plurality of terminals may also be employed) and defines the relationships between these factors (hereinafter called a relation), which establishes validation rules for groups of the factors. The researcher may also enter constraints and a parameter specifying the degree of factor interaction for each relation. Display controller 12 stores the factor relations and validation rules in a relation database 18. Tables of experimental runs for each relation are generated in a process 14 and then stored also in database 18. After all data are entered, the factor relationships defined and individual tables of experimental runs generated, the researcher requests generation of a consolidated table of experimental runs. The experimental run script merger process 20 then generates a single table of runs combining the tables of runs generated by process 16. The resulting table of experimental runs is stored in database 22 for subsequent use by the researcher.

The system described above implements a method for enumerating a minimal number of experimental runs. The method comprises two general sets of procedures—one for generating a table of experimental runs for each individual relation as embodied in process 14 and another for combining the individual tables into a single table as embodied in process 20. The building blocks used in each set of procedures are the factors, factor identities, relations and degree of factor interactions entered by the researcher.

To create a relation, the researcher specifies the factors in the relation, a set of identities for each factor and constraints. The factors specified can come from one screen or from a plurality of screens. Once the researcher specifies the relationships among factors and identities, the researcher also specifies the degree of interaction between factors to test the interactions as an n-combination (e.g. pair-wise, triples, exhaustive, etc.). As an example, pair wise combinations mean that for any two factors $f_1$ and $f_2$ and any valid identities, $v_1$ for f and $v_2$ for $f_2$, there is some experimental run in which $f_1$ has the value $v_1$ and $f_2$ has the value $v_2$.

The invention can use a set of procedures based on deterministic algorithms in combination with a set of procedures based on a random algorithm. A deterministic algorithm is a process in which a correct next step is determined only by a current state. If a deterministic process is repeated from a fixed initial state it will yield the same outcome. A standard mathematical process such as a sequence of addition and multiplication is an example of a deterministic process. A random algorithm is a process that is at least partially governed by chance. Repetition of a random process from a fixed initial state will not yield the same outcome. A statistical process such as roulette is an example of a random process.

In an exemplary embodiment of generation process 14, deterministic procedures are used first to attempt to produce a table. If deterministic procedures cannot directly be used because the number of factors and interactions are not conducive to a deterministic approach, then the relation is decomposed into sub-parts for which experimental runs can be generated using deterministic procedures. Process 14 uses the generated experimental runs for the sub-parts as seed experimental runs for a random procedure that generates a table of experimental runs for that relation.

The first step in the deterministic process is to examine a relation and determine the group of factors with the largest number of factor identities or the largest group of factors with the same number of factor identities. The next step is to examine the group of factors to determine if a table of experimental runs can be generated using a deterministic algorithm.

In this embodiment, the deterministic algorithm can be a projective plane procedure, application of the general product rule procedure or just an exhaustive enumeration of all combinations of factor identities. If only one factor exists with the largest number of factor identities, the deterministic procedure simply generates all n-way combinations (where n is the degree of interaction) for a selected subset of factors with the highest number of factor identities using art-recognized techniques of exhaustive enumeration. In an exhaustive enumeration, all possible outcomes are generated from a mathematical algorithm. This is typically done by various applications of well known techniques of permutation and combination to lists of input variables. For example, suppose a baseball manager wishes to try all possible batting orders for a team of 9 men in successive games. How many games are required to try all orders? An exhaustive enumeration uses all permutations of 9 members taken 9 at a time, or 9P9=9! (9factorial)=9×8×7×6×5×4×3×2×1=363,880 ball games.

Experimental runs nominated by the deterministic procedure can be compared with experimental runs nominated from a projective plane or product rule procedure from a subset of the relation with the largest number of factors having common identities. The resulting subset of factors can be used to seed (enter the initial values in the table for the algorithm) the random algorithm that is used for completing the table by filling in identities for the remaining factors.

A generalized projective plane procedure can be used when the number of identities is a fixed prime power q and the number of factors is q+1. A projective plane is defined as an array of points and lines with the following geometric properties:

Any two distinct points are incident with exactly one line.

Any two distinct lines are incident with exactly one point

There exist four points with not three on a single line.

See A. Beutelspacher, in The CRC Handbook of Combinatorial Designs, C. J. Colbourn and J. H. Dinitz, eds, CRC Press, New York, 1996, p 694.

A projective plane is equivalent to the common experimental design known as "Mutually Orthogonal Latin Squares" (ibid, p 113). The generalized projective plane construction gives a table of qn experimental runs where q is the number of factor identities and n is the degree of interaction and $n \leq q+1$. An example where q=3 is given in the following merged RELATION TABLES exemplifying a chemical system. RELATION TABLES

TABLE 1

| | Factors (q + 1 = 4) Metal | Halide | Solvent | Complexing Agent |
|---|---|---|---|---|
| Identities | Cr | Cl | DMA | Diglyme |
| (q = 3) | Cu | Br | DEA | Triglyme |
| | Co | I | DBA | Tetraglyme |

TABLE 2

PROJECTIVE PLANE (LATIN SQUARE) DESIGN

| Run | Metal | Halide | Solvent | Complexing Agent |
|---|---|---|---|---|
| 1 | Cr | Cl | DMA | Diglyme |
| 2 | Cr | Br | DEA | Triglyme |
| 3 | Cr | I | DBA | Tetraglyme |
| 4 | Cu | Cl | DEA | Tetraglyme |
| 5 | Cu | Br | DBA | Diglyme |
| 6 | Cu | I | DMA | Triglyme |
| 7 | Co | Cl | DBA | Triglyme |
| 8 | Co | Br | DMA | Tetraglyme |
| 9 | Co | I | DEA | Diglyme |

The generalized projective plane procedures develop n-way coverage as follows. The number of experimental runs necessary to cover n-way interactions of q number of factor identities is $q^n$. The procedure then lists the number of n-way combinations as $(\alpha_1, \ldots, \alpha_n)$ with $(0, \ldots, 0)$ being the first and $(n-1, \ldots, n-1)$ being the last. The process then determines experimental runs of the form $(a_1, \ldots a_f)$, with f being the number of factors. For $\lambda$ from 0 to q, the value (modulus q) is the value at factor $\lambda$ for an experimental run labeled $(\alpha_1, \ldots, \alpha_n)$. If $f=q^{+1}$, then the value for $a_f$ is $\alpha_n$. The factor $q^{+1}$ is called the "line at infinity." For the situation when q is a prime power but not a prime number, identification needs to be made between numbers 1 to q and the finite factor with q elements.

Figure 4:
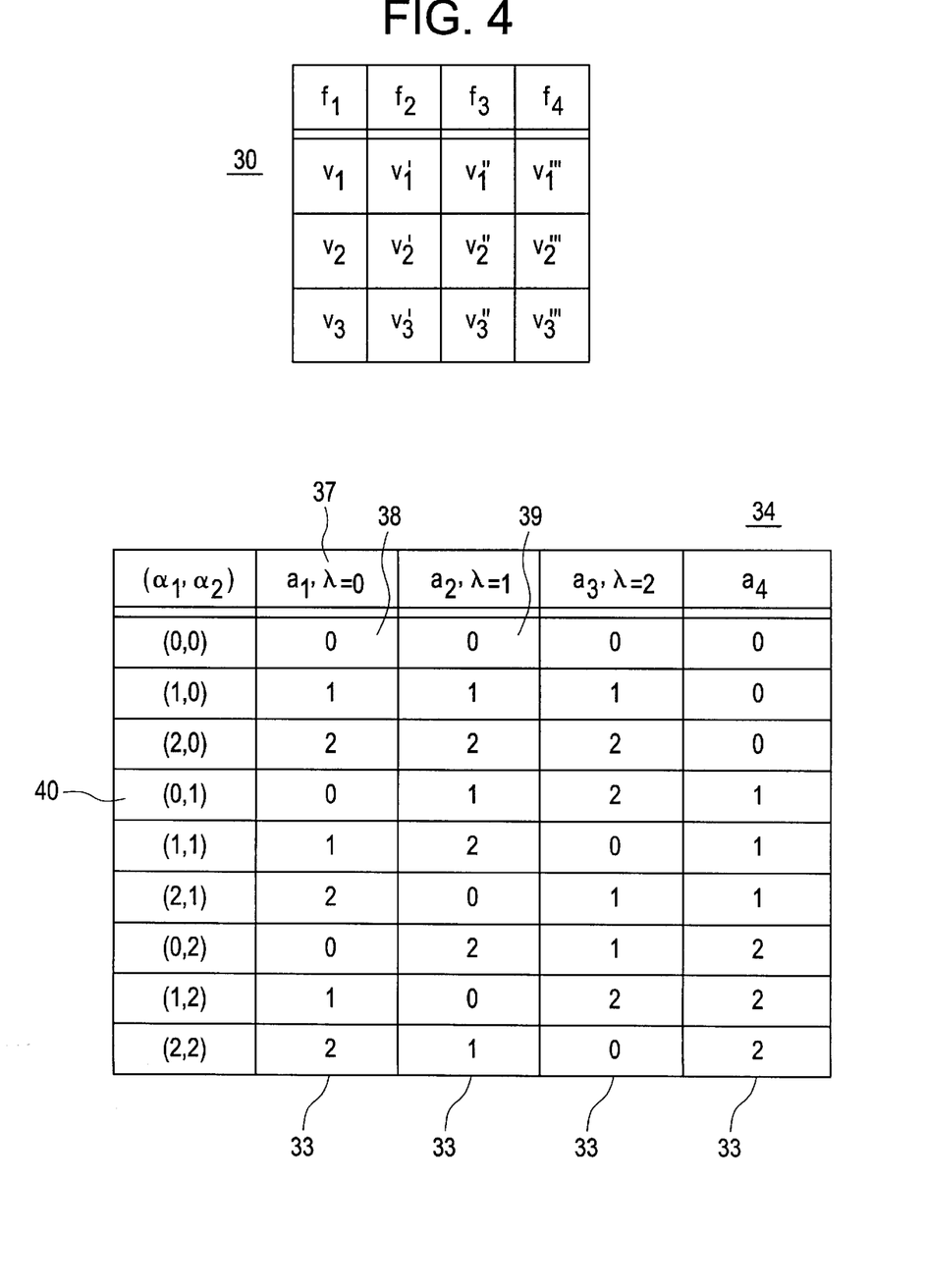
FIGS. 4 and 5 are TABLES of experimental runs for individual relationships of an experimental space.

As an example of applying the procedure to a relation, assume the chemical relation shown in the RELATION TABLE with four factors each with three identities. This chemical relation is equivalent to the mathematical relation 30 as shown in FIG. 4. Further, assume that the researcher wishes to generate experimental runs for pair-wise combinations of the factors. The process numbers the experimental runs according to the number of pair wise combinations that can be generated. With three levels of identities for each factor, the number of pair wise combinations (n=2) that can be generated is nine ($3^2$). Therefore, the following formula is used to generate the first of nine experimental runs of the form $(a_1, a_2, a_3, a_4)$ for pair-wise interactions:

Here a is the first value of the first pair 36 and $\lambda$ is a number representing the factor position 37 from the vector $(1, \ldots, q)$ representing the number of factors. Therefore, the value for $a_1$ is $\alpha_1$ times $\lambda^{1-1}$ plus $\alpha_2$ times $\lambda^{2-1}$ at factor 1 ($\lambda=0$), which equals 0 shown at 38. The value for $a_2$ is $\alpha_2$ times $\lambda^{1-1}$ plus $\alpha_2$ times $\lambda^{2-1}$ at factor 2 ($\lambda=1$), which is also 0 shown at 39. This process is repeated for each $a_i$ for each of the nine experimental runs.

The resultant table 34 in FIG. 4 shows nine experimental runs as shown in FIG. 4. In the table 34, each of the columns 33 represents a factor and each number in each cell within each column represents a factor identity. For example, in the fourth experimental run labeled (0,1) 40, the 0 under the column $a_1$ indicates the first factor value for factor 1 and the 2 under column $a_3$ indicates the third value for factor 3. Accordingly, the fourth experimental run shown in table 34 for relation 30 is $(V_1, v_2', v_3, v_2')$. The equivalent chemical result is shown in Table 2 of the RELATION TABLES.

A projective plane algorithm is only directly applicable when the number of factor identities is q (a prime or power of prime) and the number of factors is less than or equal to q+1. Although the algorithm is also effective when the number of identities is close to a prime power, for example 10 is close to 11. Often a relation does not easily fit the projective plane construct. Under these circumstances, the experimental run enumeration process breaks the relation into sub-relations to determine if experimental runs for a sub-relation can be generated deterministically, either using the projective plane procedure or, if the sub-relation is small enough, through exhaustive enumeration. If so, the subrelations (subsets) are then merged using product rules.

A product rule is defined as a process in which two tables of experimental runs are merged by repetition of each of the elements in the first table by the number of the factors in the second table and then each of the sequence of elements for the factors in the second table is repeated by the number of factors in the first table. Duplicate rows in the resultant table are then eliminated. The product rules are only directly applicable whenever each factor has the same number of factor identities and the degree of factor interaction is pair-wise.

Figure 5:
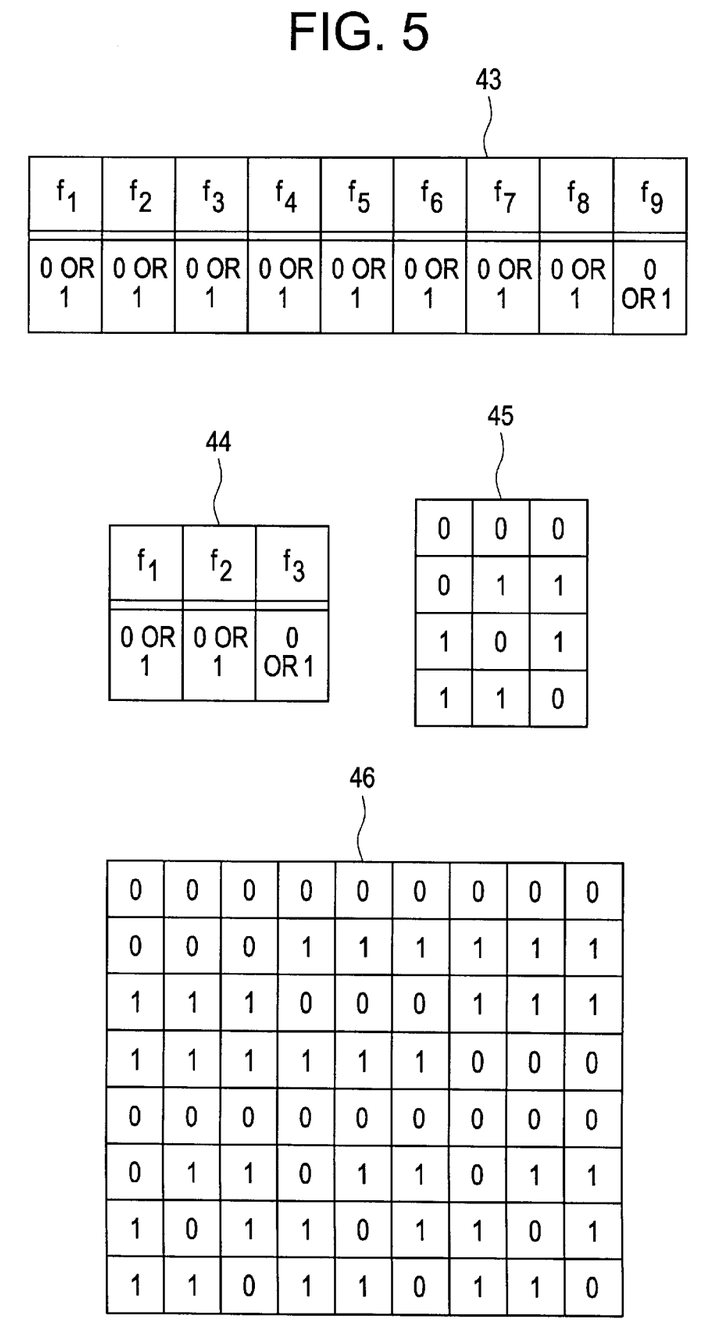

As an example, consider a relation 43 shown in FIG. 5 having 9 factors each with two factor identities. In the process, a subset of the relation 44 is taken for which the projective plane algorithm can be applied. Experimental runs are generated for the subset. In this example, experimental runs 45 were generated for relation 44 for pair wise coverage of three factors each with two factor identities. The product rules produce a table of 8 experimental runs for nine factors 46. These experimental runs 46 are the products of experimental runs 45 combined with themselves. The process for doing so is to repeat each of the elements in the first table by the number of factors in the second table and then repeat each of the sequence of elements for the factors in the second table by the number of factors in the first table. The process then examines the resulting table of experimental runs to eliminate duplicates. In the example above, the fifth experimental run 42 is a duplicate of the first experimental run 41 and is removed.

Implementation of the product rules can be generalized as follows. Let S and T be two sets of experimental runs with the same number of identities for each factor. The number of factors may vary. As an example, let S have m factors and T have r factors. A typical experimental run in S would be written as $(s_j, \ldots, s_m)$. A typical experimental run for T would be written as $(t_1, \ldots, t_r)$. The product of experimental runs for m*r factors would be of the form $(s_1, \ldots, s_1, s_2, \ldots, s_2, \ldots s_m, \ldots s_m)$ repeated r times for each $s_i$ and $(t_1, \ldots, t_1, \ldots, t_1, \ldots, T_r)$ where each experimental run $(t_1, \ldots, t_r)$ is repeated m times.

A random procedure can be used to complete the generation of a table of experimental runs when the deterministic procedures cannot be used to generate a complete table of experimental runs for a relation. For each new experimental run, the random procedure begins by generating a set of candidate experimental runs using the locally greedy algorithm described below. Given this set of candidate experimental runs, the algorithm picks the next experimental run using an evaluation function, which assigns a score to each candidate experimental run. The experimental run added to the table is the candidate experimental run with the highest score. The two basic evaluation functions are the "edge-greedy" evaluation function and the "balanced greedy" evaluation function.

The basic steps that comprise the locally greedy algorithm are as follows:

1. Select a (n−1) set (n=the degree of interaction) that has the highest priority. Use random selection in the case of ties. For example, in the case of pair-wise coverage, the set would be a factor and value combination that has the greatest number of uncovered pairs (pair-wise combinations of identities which are not included in one of the experimental runs generated by the deterministic procedure).
2. Select at random an order for the remaining factors. Working in that order, for each factor, find the factor identities that give the highest score with respect to the evaluation function selected by the researcher for the run. The evaluation function, may for example, score by counting the number of additional uncovered pairs which would be covered if that identity was selected. Choose the highest scored identity (at random if ties occur) and proceed to the next factor.
3. After an identity has been chosen for each factor, check that the set of factor identities contains none of the combinations of experimental runs, which the experimenter does not want to examine (constraints). If the resulting set of factor identities violates a constraint, then permute (interchange) the factor labels (e.g. $f_1, f_2, f_3, f_4$ in FIG. 4) as they are associated with the specified identities and see if the resultant experimental run violates the constraint. If this does not work, discard the set of factor identities and generate another. If none of the generated experimental runs satisfies the constraints, the locally greedy algorithm uses an exhaustive search to find an experimental run. If a constraint does not rule out a large percentage of the experimental runs, one of the generated sets of factor identities is likely to satisfy it.

The balanced greedy algorithm is another method of generating a table. For pair-wise coverage defined above the balanced greedy algorithm uses the following:

If (f,i), where f is a field and i is an identity, is defined as a point in space, a space of a table can be defined as the set of uncovered pairs (connections between all points (f,i) and (f',i') where that pair has not already been covered in an experimental run).

A potential function can be assigned to each point in the space as follows:

Assign each point a tuple $(n_a, \ldots n_v)$ where v is the number of factors and $n_a$ is the number of uncovered pairs $\{(f,i), (a,i')\}$ in the space Calculate the sum of squares of the entries in the tuple.

A steepest descent method can then be used to find the greatest decrease in the potential function from point to point, to determine a minimal set of runs. In this method, starting from an initial point (f,I), the value of the potential function is determined at all the points connected to that point (as defined above). The point (f',i') with the largest value of the potential function is selected and a run containing the pair of identities (i,i') for fields (f,f') is added to the table. The process is then reiterated from the point (f',i') and continued until no uncovered pairs remain.

A researcher can then specify constraints that are used by the method as unallowed experimental runs. A set of unallowed experimental runs can be specified using explicit identities (the exact identity for each factor in a run is specified) or "wild cards," (exact identities are not specified but values vary freely). Other runs may be specified by the experimenter as unallowed even though they would be valid by all the rules heretofore specified. For example, if a researcher specifies an experimental run that should not happen, that experimental run is removed from the test set.

In another embodiment, the relations defined above are used in an experimental run merging process 20 that merges individual tables of experimental runs generated for each relation in accordance with the rules that follow:

1. If two or more relations have factors in common, the merged test set for them is the union of the test sets for the individual relations; and
2. For those relations that do not have factors in common, a merged test set is created by folding the smaller test set into the larger. In the folding process the smaller test set is replicated until it is equal in number of rows of the larger test set (truncating the last replication if necessary) and columns of the resulting test set are added next to columns of the larger test set.

Also, a researcher can specify seed experimental runs for each relation. Seed experimental runs can be either required or unallowable. Required seed cases will be guaranteed to be in the final set, while unallowable seed experimental runs are guaranteed not to appear in a final test set. Unallowed seed experimental runs are treated as constraints, while required seed experimental runs are used to seed the random greedy algorithm. Since some of the n-way combinations are already covered in the seed required cases, the system produces fewer additional experimental runs.

In another aspect of the invention, a group of factors can be selected and that group defined as virtual factors (hereinafter called complexes). These complexes are used with other factors to defined a relation to be processed by the method. In processing, a complex is treated like a singular factor. These relations including complexes can be stored in database 18 and used by the system as a singular factor to be built into relations for the process.

Figure 6:
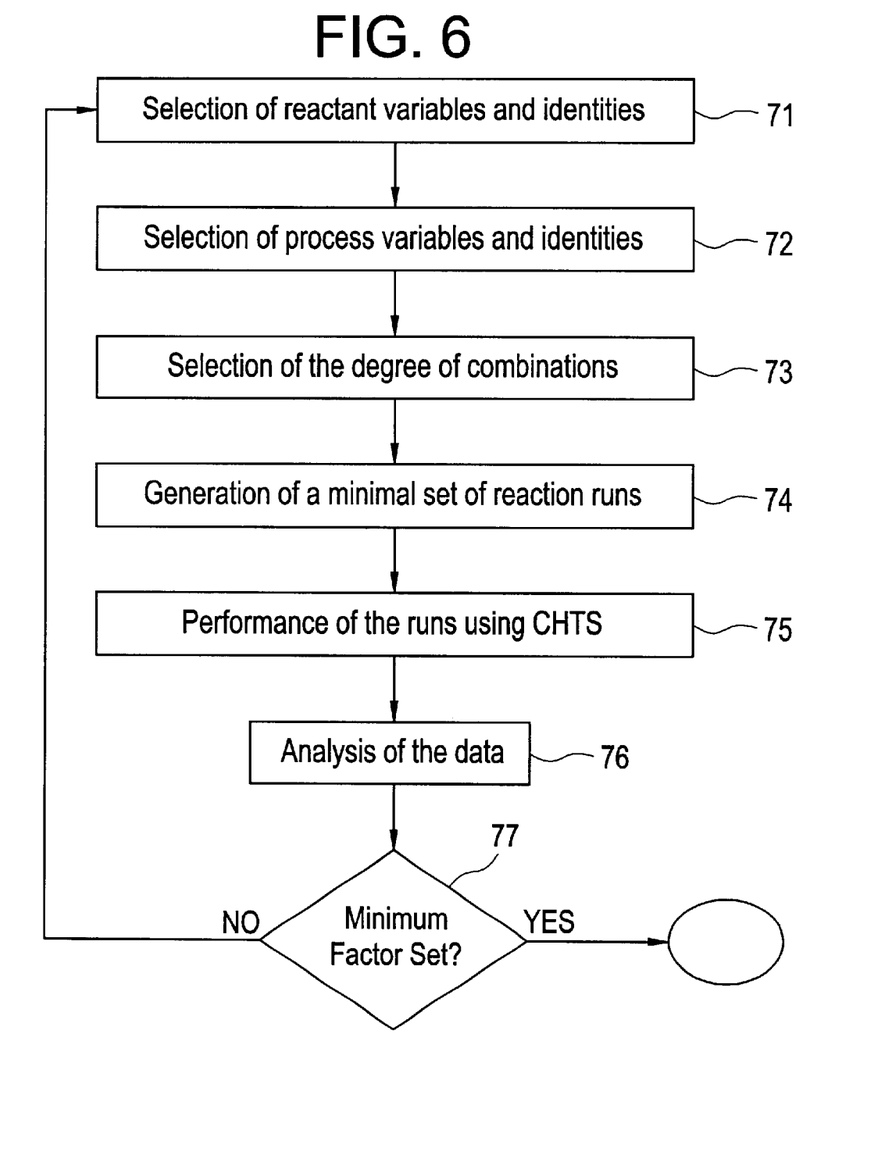
FIG. 6 is a schematic representation of a method and system for selecting a best case set of factors for a chemical reaction.

Many important chemical reactions are based on numerous factors of reactants, catalysts and conditions. The present invention can be used to select a best case set of factors of such reactions or as part of a synthesis procedure to carry out such reactions. In one embodiment, the invention comprises generating varying sets of chemical reaction factors and testing the sets by a high throughput screening process such as CHTS. FIG. 6 is a schematic representation illustrating a method and system for a selecting best case set of factors for a chemical reaction.

Referring to FIG. 6, an appropriate set of reactant variables and their identities 71; a set of process variables and their identities 72 and a degree of interaction or combination (e.g. 2-way, 3-way) 73 are selected. A minimal set of reaction runs is generated 74 and the runs are performed 75 by a CHTS method. The resulting data are analyzed 76 with graphical and statistical tools to determine a set of factors and identities, which provide the best result from the reaction. A determination is made as to whether the determined set of factors and identities is actually a minimal set. If not, the process is reiterated using a reduced set of factors as determined in the first iteration.

In an embodiment, the invention is directed to a sampling protocol for a CHTS method and system. The method and system of the present invention can be useful for parallel high-throughput screening of chemical reactants, catalysts, and related process conditions. The method and system allows researchers to investigate a complex experimental space defined by two or more factors having multiple possible identities.

Typically, a CHTS method is characterized by parallel reactions at a micro scale. In one aspect, CHTS can be described as a method comprising (A) an iteration of steps of (i) selecting a set of reactants; (ii) reacting the set and (iii) evaluating a set of products of the reacting step and (B) repeating the iteration of steps (i), (ii) and (iii) wherein a successive set of reactants selected for a step (i) is chosen as a result of an evaluating step (iii) of a preceding iteration.

In another typical CHTS method, a multiplicity of tagged reactants is subjected to an iteration of steps of (A) (i) simultaneously reacting the reactants, (ii) identifying a multiplicity of tagged products of the reaction and (B) evaluating the identified products after completion of a single or repeated iteration (A).

A typical CHTS can utilize advanced automated, robotic, computerized and controlled loading, reacting and evaluating procedures.

In one embodiment, the invention is applied to study a process for preparing diaryl carbonates. Diaryl carbonates such as diphenyl carbonate can be prepared by reaction of hydroxyaromatic compounds such as phenol with oxygen and carbon monoxide in the presence of a catalyst composition comprising a Group VIIIB metal such as palladium or a compound thereof, a bromide source such as a quaternary ammonium or hexaalkylguanidinium bromide and a polyaniline in partially oxidized and partially reduced form. The invention can be applied to screen for a catalyst to prepare a diaryl carbonate by carbonylation.

Various methods for the preparation of diaryl carbonates by a carbonylation reaction of hydroxyaromatic compounds with carbon monoxide and oxygen have been disclosed. The carbonylation reaction requires a rather complex catalyst. Reference is made, for example, to Chaudhari et al., U.S. Pat. No. 5,917,077.

The catalyst compositions described therein comprise a Group VIIIB metal (i.e., a metal selected from the group consisting of ruthenium, rhodium, palladium, osmium, iridium and platinum) or a complex thereof.

The catalyst material also includes a bromide source. This may be a quaternary ammonium or quaternary phosphonium bromide or a hexaalkylguanidinium bromide. The guanidinium salts are often preferred; they include the α, ω-bis (pentaalkylguanidinium)alkane salts. Salts in which the alkyl groups contain 2–6 carbon atoms and especially tetra-n-butylammonium bromide and hexaethylguanidinium bromide are particularly preferred.

Other catalytic constituents are necessary in accordance with Chaudhari et al. The constituents include inorganic cocatalysts, typically complexes of cobalt(II) salts with organic compounds capable of forming complexes, especially pentadentate complexes. Illustrative organic compounds of this type are nitrogen-heterocyclic compounds including pyridines, bipyridines, terpyridines, quinolines, isoquinolines and biquinolines; aliphatic polyamines such as ethylenediamine and tetraalkylethylenediamines; crown ethers; aromatic or aliphatic amine ethers such as cryptanes; and Schiff bases. The especially preferred inorganic cocatalyst in many instances is a cobalt(II) complex with bis-3-(salicylalamino)propylmethylamine.

Organic cocatalysts may be present. These cocatalysts include various terpyridine, phenanthroline, quinoline and isoquinoline compounds including 2,2':6',2"-terpyridine, 4-methylthio-2,2':6',2"-terpyridine and 2,2':6',2"-terprridine N-oxide, 1,10-phenanthroline, 2,4,7,8-tetramethyl-1,10-phenanthroline, 4,7-diphenyl-1,10, phenanthroline and 3,4, 7,8-tetramethy-1,10-phenanthroline. The terpyridines and especially 2,2':6',2"-terpyridine are preferred.

Another catalyst constituent is a polyaniline in partially oxidized and partially reduced form.

Any hydroxyaromatic compound may be employed. Monohydroxyaromatic compounds, such as phenol, the cresols, the xylenols and p-cumylphenol are preferred with phenol being most preferred. The method may be employed with dihydroxyaromatic compounds such as resorcinol, hydroquinone and 2,2-bis(4-hydroxyphenyl)propane or "bisphenol A," whereupon the products are polycarbonates.

Other reagents in the carbonylation process are oxygen and carbon monoxide, which react with the phenol to form the desired diaryl carbonate.

These and other features will become apparent from the following detailed discussion, which by way of example without limitation describes a preferred embodiment of the present invention.

EXAMPLE

This example illustrates an identification of an active and selective catalyst for the production of aromatic carbonates. The Example identifies the best catalyst from a complex chemical space, where the chemical space is defined as an assemblage of all possible experimental conditions defined by a set of variable parameters such as formulation ingredient identity or amount or a process parameter such as reaction time, temperature or pressure. The chemical space consists of the following chemical components and process parameters from TABLE 3 and TABLE 4:

TABLE 3

| Factor | Possible Identities | Possible Identities |
|---|---|---|
| Primary Catalyst | Ru(acac)$^3$ | All at 25 ppm |
|  | Pt(acac)$^2$ |  |
|  | Rh(acac)$^3$ |  |
|  | Ir(acac)$^3$ |  |
| Metal Cocatalyst | Mn(acac)$^2$ | 150 and 1500 ppm |
|  | Fe(acac)$^3$ |  |
|  | Co(acac)$^2$ |  |
|  | Ce(acac)$^3$ |  |

TABLE 3-continued

| Factor | Possible Identities | Possible Identities |
|---|---|---|
| Cosolvent | Dimethylformamide (DMFA), Dimethylacetamide (DMAA), Tetrahydrofuran (THF), Diglyme (DiGly) | All at 10% |
| Anion Cocatalyst | Cl, Br, I, Cn (as hexamethylguanadinium salts) | 500 and 5000 ppm |

TABLE 4

| Factor | Possible Identities |
|---|---|
| Pressure | 1000 psi, 1500 psi (8% Oxygen in Carbon Monoxide) |
| Temperature | 100 C, 120 C |
| Reaction time | 120 min, 180 min |

The next step in the Example is to determine if unusually good results could occur in the system as a result of three-way combinations. The system has four factors with four identities each (Primary catalyst, Metal Cocatalyst, Cosolvent and Anion Cocatalyst) and five factors with two identities each (Metal Cocatalyst amount, Anion Cocatalyst amount, Pressure, Temperature, and Reaction Time). There are $4^4 \times 2^5 = 8192$ possible combinations of these factors. All three-way combinations of the factors are examined in 128 runs, as shown in the following TABLE 5

TABLE 5

| Run | Primary Catalyst | Amount (ppm) | Metal Cocatalyst | Amount (ppm) | Solvent | Amount (%) | Anlon Cocatalyst | Anlon Cocatalyst Amount | Pressure (psi) | Temperature (C.) | Reaction Time (min) | TON |
|---|---|---|---|---|---|---|---|---|---|---|---|---|
| 1 | Ru(acac)3 | 25 | Mn(acac)2 | 1500 | DMFA | 10 | Cl— | 5000 | 1000 | 100 | 180 | 118.2 |
| 2 | Ru(acac)3 | 25 | Mn(acac)2 | 150 | DMAA | 10 | Br— | 5000 | 1000 | 120 | 180 | 134.6 |
| 3 | Ru(acac)3 | 25 | Mn(acac)2 | 1500 | THF | 10 | I— | 5000 | 1500 | 120 | 180 | 124.1 |
| 4 | Ru(acac)3 | 25 | Mn(acac)2 | 1500 | Digly | 10 | CN— | 5000 | 1000 | 120 | 120 | 134.8 |
| 5 | Ru(acac)3 | 25 | Fe(acac)3 | 150 | DMFA | 10 | Br— | 500 | 1500 | 120 | 180 | 185.1 |
| 6 | Ru(acac)3 | 25 | Fe(acac)3 | 1500 | DMAA | 10 | I— | 500 | 1000 | 100 | 120 | 31.9 |
| 7 | Ru(acac)3 | 25 | Fe(acac)3 | 1500 | THF | 10 | CN— | 500 | 1500 | 120 | 120 | 311.8 |
| 8 | Ru(acac)3 | 25 | Fe(acac)3 | 1500 | Digly | 10 | Cl— | 500 | 1500 | 100 | 180 | 328.3 |
| 9 | Ru(acac)3 | 25 | Co(acac)2 | 1500 | DMFA | 10 | I— | 500 | 1000 | 120 | 180 | 1138.2 |
| 10 | Ru(acac)3 | 25 | Co(acac)2 | 150 | DMAA | 10 | CN— | 5000 | 1500 | 120 | 120 | 275.1 |
| 11 | Ru(acac)3 | 25 | Co(acac)2 | 150 | THF | 10 | Cl— | 5000 | 1500 | 100 | 180 | 241.1 |
| 12 | Ru(acac)3 | 25 | Co(acac)2 | 150 | Digly | 10 | Br— | 500 | 1000 | 100 | 180 | 392.0 |
| 13 | Ru(acac)3 | 25 | Ce(acac)3 | 150 | DMFA | 10 | CN— | 500 | 1000 | 120 | 120 | 80.3 |
| 14 | Ru(acac)3 | 25 | Ce(acac)3 | 150 | DMAA | 10 | Cl— | 500 | 1500 | 100 | 120 | 98.0 |
| 15 | Ru(acac)3 | 25 | Ce(acac)3 | 1500 | THF | 10 | Br— | 5000 | 1500 | 100 | 120 | 347.0 |
| 16 | Ru(acac)3 | 25 | Ce(acac)3 | 150 | Digly | 10 | I— | 5000 | 1000 | 100 | 120 | 400.7 |
| 17 | Pt(acac)2 | 25 | Mn(acac)2 | 1500 | DMFA | 10 | Br— | 5000 | 1000 | 100 | 180 | 228.6 |
| 18 | Pt(acac)2 | 25 | Mn(acac)2 | 150 | DMAA | 10 | I— | 5000 | 1000 | 120 | 180 | 345.2 |
| 19 | Pt(acac)2 | 25 | Mn(acac)2 | 1500 | THF | 10 | CN— | 5000 | 1500 | 120 | 180 | 216.1 |
| 20 | Pt(acac)2 | 25 | Mn(acac)2 | 1500 | Digly | 10 | Cl— | 5000 | 1000 | 120 | 120 | 419.8 |
| 21 | Pt(acac)2 | 25 | Fe(acac)3 | 150 | DMFA | 10 | I— | 500 | 1500 | 120 | 180 | 218.3 |
| 22 | Pt(acac)2 | 25 | Fe(acac)3 | 1500 | DMAA | 10 | CN— | 500 | 1000 | 100 | 120 | 205.2 |
| 23 | Pt(acac)2 | 25 | Fe(acac)3 | 1500 | THF | 10 | Cl— | 500 | 1500 | 120 | 120 | 347.1 |
| 24 | Pt(acac)2 | 25 | Fe(acac)3 | 1500 | Digly | 10 | Br— | 500 | 1500 | 100 | 180 | 311.0 |
| 25 | Pt(acac)2 | 25 | Co(acac)2 | 1500 | DMFA | 10 | CN— | 500 | 1000 | 120 | 180 | 231.9 |
| 26 | Pt(acac)2 | 25 | Co(acac)2 | 150 | DMAA | 10 | Cl— | 5000 | 1500 | 120 | 120 | 226.8 |
| 27 | Pt(acac)2 | 25 | Co(acac)2 | 150 | THF | 10 | Br— | 5000 | 1500 | 100 | 180 | 200.2 |
| 28 | Pt(acac)2 | 25 | Co(acac)2 | 150 | Digly | 10 | I— | 500 | 1000 | 100 | 180 | 332.2 |
| 29 | Pt(acac)2 | 25 | Ce(acac)3 | 150 | DMFA | 10 | Cl— | 500 | 1000 | 120 | 120 | 195.1 |
| 30 | Pt(acac)2 | 25 | Ce(acac)3 | 150 | DMAA | 10 | Br— | 500 | 1500 | 100 | 120 | 313.9 |
| 31 | Pt(acac)2 | 25 | Ce(acac)3 | 1500 | THF | 10 | I— | 5000 | 1500 | 100 | 120 | 403.6 |
| 32 | Pt(acac)2 | 25 | Ce(acac)3 | 150 | Digly | 10 | CN— | 5000 | 1000 | 100 | 120 | 362.1 |
| 33 | Rh(acac)3 | 25 | Mn(acac)2 | 1500 | DMFA | 10 | I— | 5000 | 1000 | 100 | 180 | 244.9 |
| 34 | Rh(acac)3 | 25 | Mn(acac)2 | 150 | DMAA | 10 | CN— | 5000 | 1000 | 120 | 180 | 224.3 |
| 35 | Rh(acac)3 | 25 | Mn(acac)2 | 1500 | THF | 10 | Cl— | 5000 | 1500 | 120 | 180 | 274.2 |
| 36 | Rh(acac)3 | 25 | Mn(acac)2 | 1500 | Digly | 10 | Br— | 5000 | 1000 | 120 | 120 | 387.7 |
| 37 | Rh(acac)3 | 25 | Fe(acac)3 | 150 | DMFA | 10 | CN— | 500 | 1500 | 120 | 180 | 226.5 |
| 38 | Rh(acac)3 | 25 | Fe(acac)3 | 150 | DMAA | 10 | Cl— | 500 | 1000 | 100 | 120 | 237.7 |
| 39 | Rh(acac)3 | 25 | Fe(acac)3 | 1500 | THF | 10 | Br— | 500 | 1500 | 120 | 120 | 290.4 |
| 40 | Rh(acac)3 | 25 | Fe(acac)3 | 1500 | Digly | 10 | I— | 500 | 1500 | 100 | 180 | 622.4 |
| 41 | Rh(acac)3 | 25 | Co(acac)2 | 1500 | DMFA | 10 | Cl— | 500 | 1000 | 120 | 180 | 386.0 |
| 42 | Rh(acac)3 | 25 | Co(acac)2 | 150 | DMAA | 10 | Br— | 5000 | 1500 | 120 | 120 | 382.0 |
| 43 | Rh(acac)3 | 25 | Co(acac)2 | 150 | THF | 10 | I— | 5000 | 1500 | 100 | 180 | 325.1 |
| 44 | Rh(acac)3 | 25 | Co(acac)2 | 150 | Digly | 10 | CN— | 500 | 1000 | 100 | 180 | 379.1 |
| 45 | Rh(acac)3 | 25 | Ce(acac)3 | 150 | DMFA | 10 | Br— | 500 | 1000 | 120 | 120 | 271.7 |
| 46 | Rh(acac)3 | 25 | Ce(acac)3 | 150 | DMAA | 10 | I— | 500 | 1500 | 100 | 120 | 382.4 |
| 47 | Rh(acac)3 | 25 | Ce(acac)3 | 1500 | THF | 10 | CN— | 5000 | 1500 | 100 | 120 | 391.5 |
| 48 | Rh(acac)3 | 25 | Ce(acac)3 | 150 | Digly | 10 | Cl— | 5000 | 1000 | 120 | 120 | 562.3 |
| 49 | Ir(acac)3 | 25 | Mn(acac)2 | 1500 | DMFA | 10 | CN— | 5000 | 1000 | 100 | 180 | 218.7 |

TABLE 5-continued

| Run | Primary Catalyst | Amount (ppm) | Metal Cocatalyst | Amount (ppm) | Solvent | Amount (%) | Anion Cocatalyst | Anion Cocatalyst Amount | Pressure (psi) | Temperature (C.) | Reaction Time (min) | TON |
|---|---|---|---|---|---|---|---|---|---|---|---|---|
| 50 | Ir(acac)3 | 25 | Mn(acac)2 | 150 | DMAA | 10 | Cl— | 5000 | 1000 | 120 | 180 | 207.6 |
| 51 | Ir(acac)3 | 25 | Mn(acac)2 | 1500 | THF | 10 | Br— | 5000 | 1500 | 120 | 180 | 271.0 |
| 52 | Ir(acac)3 | 25 | Mn(acac)2 | 1500 | Digly | 10 | I— | 5000 | 1000 | 120 | 120 | 198.2 |
| 53 | Ir(acac)3 | 25 | Fe(acac)3 | 150 | DMFA | 10 | Cl— | 500 | 1500 | 120 | 180 | 151.2 |
| 54 | Ir(acac)3 | 25 | Fe(acac)3 | 1500 | DMAA | 10 | Br— | 500 | 1000 | 100 | 120 | 228.8 |
| 55 | Ir(acac)3 | 25 | Fe(acac)3 | 1500 | THF | 10 | I— | 500 | 1500 | 120 | 120 | 232.8 |
| 56 | Ir(acac)3 | 25 | Fe(acac)3 | 150 | Digly | 10 | CN— | 500 | 1500 | 100 | 180 | 578.9 |
| 57 | Ir(acac)3 | 25 | Co(acac)2 | 1500 | DMFA | 10 | Br— | 500 | 1000 | 120 | 180 | 185.1 |
| 58 | Ir(acac)3 | 25 | Co(acac)2 | 150 | DMAA | 10 | I— | 5000 | 1500 | 120 | 120 | 424.9 |
| 59 | Ir(acac)3 | 25 | Co(acac)2 | 150 | THF | 10 | CN— | 5000 | 1000 | 100 | 180 | 471.1 |
| 60 | Ir(acac)3 | 25 | Co(acac)2 | 150 | Digly | 10 | Cl— | 500 | 1000 | 100 | 180 | 445.7 |
| 61 | Ir(acac)3 | 25 | Ce(acac)3 | 150 | DMFA | 10 | I— | 500 | 1000 | 120 | 120 | 260.9 |
| 62 | Ir(acac)3 | 25 | Ce(acac)3 | 150 | DMAA | 10 | CN— | 500 | 1500 | 100 | 120 | 284.9 |
| 63 | Ir(acac)3 | 25 | Ce(acac)3 | 1500 | THF | 10 | Cl— | 5000 | 1500 | 100 | 120 | 241.0 |
| 64 | Ir(acac)3 | 25 | Ce(acac)3 | 150 | Digly | 10 | Br— | 5000 | 1000 | 100 | 120 | 322.6 |
| 65 | Ru(acac)3 | 25 | Mn(acac)2 | 150 | DMFA | 10 | Cl— | 500 | 1500 | 120 | 120 | 128.3 |
| 66 | Ru(acac)3 | 25 | Mn(acac)2 | 1500 | DMAA | 10 | Br— | 500 | 1500 | 100 | 120 | 94.4 |
| 67 | Ru(acac)3 | 25 | Mn(acac)2 | 150 | THF | 10 | I— | 500 | 1000 | 100 | 120 | 193.6 |
| 68 | Ru(acac)3 | 25 | Mn(acac)2 | 150 | Digly | 10 | CN— | 500 | 1500 | 100 | 180 | 352.2 |
| 69 | Ru(acac)3 | 25 | Fe(acac)3 | 1500 | DMFA | 10 | Br— | 5000 | 1000 | 100 | 180 | 102.1 |
| 70 | Ru(acac)3 | 25 | Fe(acac)3 | 150 | DMAA | 10 | I— | 5000 | 1500 | 120 | 180 | 176.6 |
| 71 | Ru(acac)3 | 25 | Fe(acac)3 | 150 | THF | 10 | CN— | 5000 | 1000 | 100 | 180 | 239.6 |
| 72 | Ru(acac)3 | 25 | Fe(acac)3 | 150 | Digly | 10 | Cl— | 5000 | 1000 | 120 | 120 | 151.4 |
| 73 | Ru(acac)3 | 25 | Co(acac)2 | 150 | DMFA | 10 | I— | 5000 | 1500 | 100 | 120 | 1112.8 |
| 74 | Ru(acac)3 | 25 | Co(acac)2 | 1500 | DMAA | 10 | CN— | 500 | 1000 | 100 | 180 | 218.3 |
| 75 | Ru(acac)3 | 25 | Co(acac)2 | 1500 | THF | 10 | Cl— | 500 | 1000 | 120 | 120 | 211.5 |
| 76 | Ru(acac)3 | 25 | Co(acac)2 | 1500 | Digly | 10 | Br— | 500 | 1500 | 120 | 120 | 173.6 |
| 77 | Ru(acac)3 | 25 | Ce(acac)3 | 1500 | DMFA | 10 | CN— | 5000 | 1500 | 100 | 180 | 125.6 |
| 78 | Ru(acac)3 | 25 | Ce(acac)3 | 1500 | DMAA | 10 | Cl— | 5000 | 1000 | 100 | 180 | 295.6 |
| 79 | Ru(acac)3 | 25 | Ce(acac)3 | 150 | THF | 10 | Br— | 500 | 1000 | 120 | 180 | 178.9 |
| 80 | Ru(acac)3 | 25 | Ce(acac)3 | 1500 | Digly | 10 | I— | 500 | 1500 | 120 | 180 | 520.1 |
| 81 | Pt(acac)2 | 25 | Mn(acac)2 | 150 | DMFA | 10 | Br— | 500 | 1500 | 120 | 120 | 97.4 |
| 82 | Pt(acac)2 | 25 | Mn(acac)2 | 1500 | DMAA | 10 | I— | 500 | 1500 | 100 | 120 | 220.4 |
| 83 | Pt(acac)2 | 25 | Mn(acac)2 | 150 | THF | 10 | CN— | 500 | 1000 | 100 | 120 | 325.5 |
| 84 | Pt(acac)2 | 25 | Mn(acac)2 | 150 | Digly | 10 | Cl— | 500 | 1500 | 100 | 180 | 428.7 |
| 85 | Pt(acac)2 | 25 | Fe(acac)3 | 1500 | DMFA | 10 | I— | 5000 | 1000 | 100 | 120 | 180.1 |
| 86 | Pt(acac)2 | 25 | Fe(acac)3 | 150 | DMAA | 10 | CN— | 5000 | 1500 | 100 | 180 | 310.5 |
| 87 | Pt(acac)2 | 25 | Fe(acac)3 | 150 | THF | 10 | Cl— | 5000 | 1000 | 100 | 180 | 300.3 |
| 88 | Pt(acac)2 | 25 | Fe(acac)3 | 150 | Digly | 10 | Br— | 5000 | 1000 | 120 | 120 | 251.4 |
| 89 | Pt(acac)2 | 25 | Co(acac)2 | 150 | DMFA | 10 | CN— | 5000 | 1500 | 100 | 120 | 244.9 |
| 90 | Pt(acac)2 | 25 | Co(acac)2 | 1500 | DMAA | 10 | Cl— | 500 | 1000 | 100 | 180 | 235.3 |
| 91 | Pt(acac)2 | 25 | Co(acac)2 | 1500 | THF | 10 | Br— | 500 | 1000 | 120 | 120 | 256.3 |
| 92 | Pt(acac)2 | 25 | Co(acac)2 | 1500 | Digly | 10 | I— | 5000 | 1500 | 120 | 120 | 335.7 |
| 93 | Pt(acac)2 | 25 | Ce(acac)3 | 1500 | DMFA | 10 | Cl— | 5000 | 1500 | 100 | 180 | 262.3 |
| 94 | Pt(acac)2 | 25 | Ce(acac)3 | 1500 | DMAA | 10 | Br— | 5000 | 1000 | 100 | 180 | 187.7 |
| 95 | Pt(acac)2 | 25 | Ce(acac)3 | 150 | THF | 10 | I— | 500 | 1000 | 120 | 180 | 517.8 |
| 96 | Pt(acac)2 | 25 | Ce(acac)3 | 1500 | Digly | 10 | CN— | 500 | 1500 | 120 | 180 | 505.8 |
| 97 | Rh(acac)3 | 25 | Mn(acac)2 | 150 | DMFA | 10 | I— | 500 | 1500 | 120 | 120 | 153.0 |
| 98 | Rh(acac)3 | 25 | Mn(acac)2 | 150 | DMAA | 10 | CN— | 500 | 1500 | 100 | 120 | 82.3 |
| 99 | Rh(acac)3 | 25 | Mn(acac)2 | 150 | THF | 10 | Cl— | 500 | 1000 | 100 | 120 | 194.1 |
| 100 | Rh(acac)3 | 25 | Mn(acac)2 | 150 | Digly | 10 | Br— | 500 | 1500 | 100 | 180 | 249.2 |
| 101 | Rh(acac)3 | 25 | Fe(acac)3 | 1500 | DMFA | 10 | CN— | 5000 | 1500 | 100 | 120 | 201.8 |
| 102 | Rh(acac)3 | 25 | Fe(acac)3 | 150 | DMAA | 10 | Cl— | 5000 | 1500 | 120 | 180 | 373.9 |
| 103 | Rh(acac)3 | 25 | Fe(acac)3 | 150 | THF | 10 | Br— | 5000 | 1000 | 100 | 180 | 337.1 |
| 104 | Rh(acac)3 | 25 | Fe(acac)3 | 150 | Digly | 10 | I— | 5000 | 1000 | 120 | 120 | 330.8 |
| 105 | Rh(acac)3 | 25 | Co(acac)2 | 150 | DMFA | 10 | Cl— | 5000 | 1500 | 100 | 120 | 95.7 |
| 106 | Rh(acac)3 | 25 | Co(acac)2 | 150 | DMAA | 10 | Br— | 500 | 1000 | 100 | 180 | 480.9 |
| 107 | Rh(acac)3 | 25 | Co(acac)2 | 1500 | THF | 10 | I— | 500 | 1000 | 120 | 180 | 389.6 |
| 108 | Rh(acac)3 | 25 | Co(acac)2 | 1500 | Digly | 10 | CN— | 5000 | 1500 | 120 | 120 | 303.0 |
| 109 | Rh(acac)3 | 25 | Ce(acac)3 | 1500 | DMFA | 10 | Br— | 5000 | 1500 | 100 | 180 | 180.9 |
| 110 | Rh(acac)3 | 25 | Ce(acac)3 | 1500 | DMAA | 10 | I— | 5000 | 1000 | 100 | 180 | 255.3 |
| 111 | Rh(acac)3 | 25 | Ce(acac)3 | 150 | THF | 10 | CN— | 500 | 1000 | 120 | 180 | 413.9 |
| 112 | Rh(acac)3 | 25 | Ce(acac)3 | 1500 | Digly | 10 | Cl— | 500 | 1500 | 120 | 180 | 497.7 |
| 113 | Ir(acac)3 | 25 | Mn(acac)2 | 150 | DMFA | 10 | CN— | 500 | 1500 | 120 | 120 | 171.3 |
| 114 | Ir(acac)3 | 25 | Mn(acac)2 | 1500 | DMAA | 10 | Cl— | 500 | 1500 | 120 | 120 | 130.3 |
| 115 | Ir(acac)3 | 25 | Mn(acac)2 | 150 | THF | 10 | Br— | 500 | 1000 | 100 | 120 | 374.4 |
| 116 | Ir(acac)3 | 25 | Mn(acac)2 | 150 | Digly | 10 | I— | 500 | 1500 | 100 | 180 | 339.4 |
| 117 | Ir(acac)3 | 25 | Fe(acac)3 | 1500 | DMFA | 10 | Cl— | 5000 | 1000 | 100 | 120 | 132.4 |
| 118 | Ir(acac)3 | 25 | Fe(acac)3 | 150 | DMAA | 10 | Br— | 5000 | 1500 | 120 | 180 | 366.0 |
| 119 | Ir(acac)3 | 25 | Fe(acac)3 | 150 | THF | 10 | I— | 5000 | 1000 | 100 | 180 | 561.2 |
| 120 | Ir(acac)3 | 25 | Fe(acac)3 | 150 | Digly | 10 | CN— | 5000 | 1000 | 120 | 120 | 192.6 |
| 121 | Ir(acac)3 | 25 | Co(acac)2 | 150 | DMFA | 10 | Br— | 5000 | 1500 | 100 | 120 | 260.0 |
| 122 | Ir(acac)3 | 25 | Co(acac)2 | 1500 | DMAA | 10 | I— | 500 | 1000 | 100 | 180 | 296.0 |
| 123 | Ir(acac)3 | 25 | Co(acac)2 | 1500 | THF | 10 | CN— | 500 | 1000 | 120 | 180 | 162.8 |
| 124 | Ir(acac)3 | 25 | Co(acac)2 | 1500 | Digly | 10 | Cl— | 5000 | 1500 | 120 | 120 | 356.6 |

TABLE 5-continued

| Run | Primary Catalyst | Amount (ppm) | Metal Cocatalyst | Amount (ppm) | Solvent | Amount (%) | Anion Cocatalyst | Anion Cocatalyst Amount | Pressure (psi) | Temperature (C.) | Reaction Time (min) | TON |
|---|---|---|---|---|---|---|---|---|---|---|---|---|
| 125 | Ir(acac)3 | 25 | Ce(acac)3 | 1500 | DMFA | 10 | I— | 5000 | 1500 | 100 | 180 | 545.8 |
| 126 | Ir(acac)3 | 25 | Ce(acac)3 | 1500 | DMAA | 10 | CN— | 5000 | 1000 | 120 | 180 | 514.9 |
| 127 | Ir(acac)3 | 25 | Ce(acac)3 | 150 | THF | 10 | Cl— | 500 | 1000 | 120 | 180 | 264.0 |
| 128 | Ir(acac)3 | 25 | Ce(acac)3 | 1500 | Digly | 10 | Br— | 500 | 1500 | 120 | 180 | 564.7 |

Catalyst mixtures are made up in phenol solvent using the concentrations of each component as given in the rows of the TABLE 5. The total volume of each catalyst mixture is 1.0 ml. From each mixture, a 25 microliter aliquot is dispensed into a 2 ml reaction vial, forming a film on the bottom. The vials are grouped on an array plate by process conditions (as specified in the Pressure, Temperature, and Reaction Time columns in TABLE 5) and each group is loaded into a high pressure autoclave and subjected to the reaction conditions specified. Thus one group, exemplified by rows number 6, 16, 22, 32, 38, 48, 54, 64, 67, 69, 83, 85, 99, 10 101, 115, 117, are all subjected to 1000 psi pressure at 100 C. for 120 min. At the end of the reaction time, the system is cooled and depressurized and the contents of each vial are analyzed for diphenyl carbonate product using conventional gas chromatographic methods. The turnover number (TON) for each reaction is calculated as (mols of diphenylcarbonate/mols of primary catalyst). The results are given in the TON column of TABLE 4.

Figure 7:
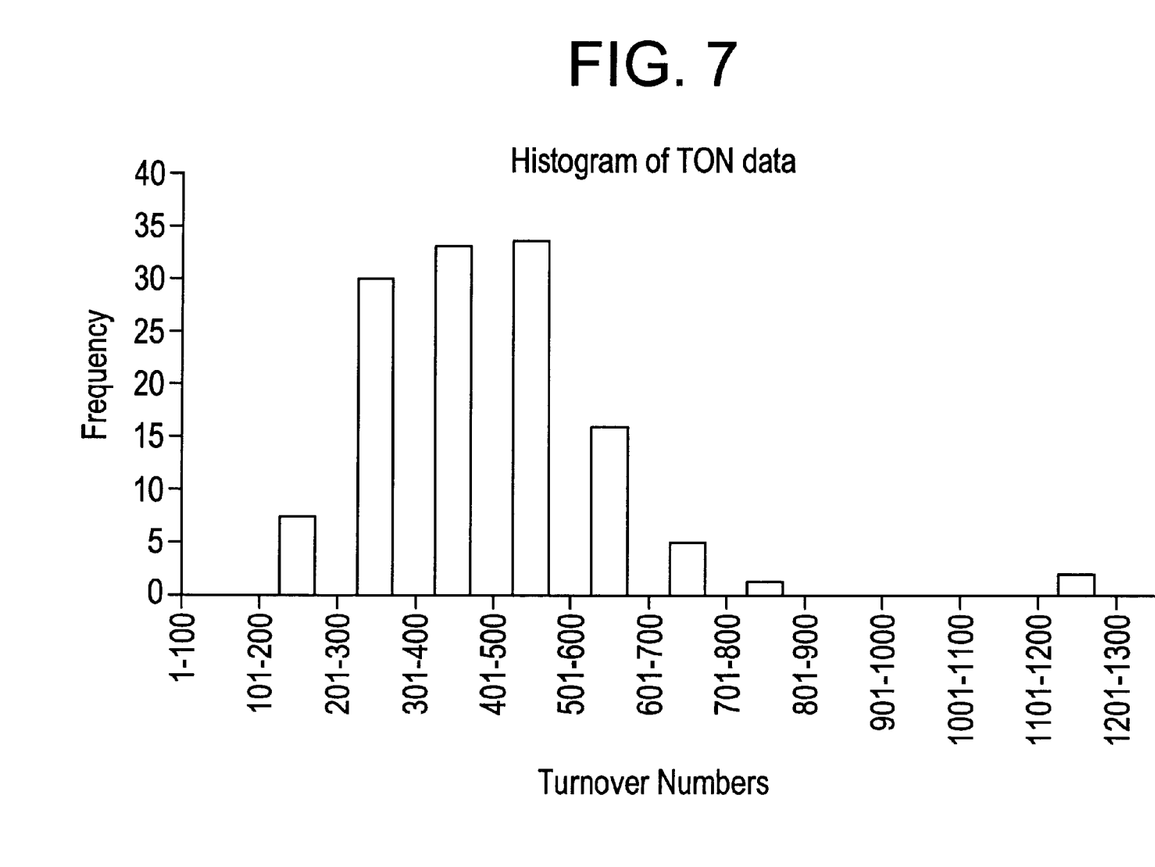
FIG. 7 is a histogram of TON results.

FIG. 7 is a histogram of the Turnover number (TON) results. FIG. 7 shows that there are two unusually high values that are associated with runs 9 and 73. Comparison of these two runs shows that they contain the combination of ingredients Ru(acac)3, Co(acac)2, DMFA, and I⁻. Further reiterations show that DMFA is not part of the combination and that the advantageous three way combination is Ru(acac)3, Co(acac)2, and I⁻.

It will be understood that each of the elements described above, or two or more together, may also find utility in applications differing from the types described herein. While the invention has been illustrated and described as experimental designs for combinatorial chemistry, it is not intended to be limited to the details shown, since various modifications and substitutions can be made without departing in any way from the spirit of the present invention. For example, various detection techniques may be coordinated with the reactions to provide data at accelerated rates. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method for selecting a best case set of factors of a chemical reaction, comprising;
   defining a chemical experimental space by (i) identifying relationships between factors of a candidate chemical reaction wherein the factors comprise a catalyst system and conditions; and (ii) determining said chemical experimental space comprising a table of test cases for each of said factors based on said identified relationships between said factors with said identified relationships based on researcher specified n-topple combinations between identities of said relationships; and
   effecting a combinatorial high throughput screening (CHTS) comprising (A) (a) reacting a reactant selected from said experimental space under a selected set of catalysts; and (b) evaluating a set of products of said reacting step to identify best sets of catalysts and reaction conditions; and (B) reiterating step (A) wherein a selected experimental space selected for a step (a) is chosen as a result of an evaluating step (b) of a preceding iteration of step (A) to select a best case set of factors from said chemical experimental space.

2. The method of claim 1, wherein said (ii) determining said chemical experimental space, comprises generating said table by a deterministic procedure.

3. The method of claim 1, wherein said (ii) determining said chemical experimental space, comprises generating said table by a random procedure.

4. The method of claim 3, wherein said random procedure comprises steps of:
   selecting at random a test case comprising a subset of cases with a number of data elements less than the total number of factors in a table and which meets a criteria of having a largest number of uncovered combinations;
   selecting in a random order the remaining factors that are not included in the data elements that are used in said subset;
   for each of said remaining factors selected, find factor identities that result in a high score when evaluated using an evaluation function;
   selecting as a generated test case to be included in said table of generated test cases said generated test case with data element identities having a high score; and
   checking that said generated test case meets all researcher defined constraints.

5. The method of claim 4, wherein said evaluation function determines a value based on a steepest descent of a potential function of a space of graphs.

6. The method of claim 1, wherein said (ii) determining said chemical experimental space, comprises generating a plurality of tables of test cases for said factors and merging said tables into a single table.

7. The method of claim 1, wherein said (ii) determining said chemical experimental space, comprises generating a plurality of tables of test cases for said factors and merging said tables into a single table by creating a union of tables whenever said tables have factors in common.

8. The method of claim 1, wherein said (ii) determining said chemical experimental space, comprises generating a plurality of tables of test cases for said factors and merging said tables into a single table by creating a union of tables whenever said tables have factors in common and folding a smaller table into a larger table of said tables whenever said tables have no factor in common.

9. The method of claim 1, wherein each factor has a plurality of possible identities.

10. The method of claim 1, wherein said CHTS comprises effecting parallel chemical reactions of an array of reactants defined as said experimental space.

11. The method of claim 1, wherein said CHTS comprises effecting parallel chemical reactions on a micro scale on reactants defined as said experimental space.

12. The method of claim 1, wherein said CHTS comprises an iteration of steps of simultaneously reacting a multiplicity of tagged reactants and identifying a multiplicity of tagged products of the reaction and evaluating said identified products after completion of a single or repeated iteration.

13. The method of claim 1, wherein said evaluating step defining a candidate chemical space for a next iteration, comprises identifying relationships between factors of said candidate chemical reaction space; and (ii) determining said chemical experimental space comprising a table of test cases for each of said factors based on said identified relationships between said factors with said identified relationships based on researcher specified n-topple combinations between identities of said relationships.

14. The method of claim 1, comprising reiterating (A) until a best set of factors of said chemical experimental space is selected.

15. The method of claim 1, wherein said chemical space includes a catalyst system comprising a Group VIII B metal.

16. The method of claim 1, wherein said chemical space includes a catalyst system comprising palladium.

17. The method of claim 1, wherein said chemical space includes a catalyst system comprising a halide composition.

18. The method of claim 1, wherein said chemical space includes an inorganic co-catalyst.

19. The method of claim 1, wherein said chemical space includes a catalyst system includes a combination of inorganic co-catalysts.

20. The method of claim 1, comprising defining the chemical experimental space by (i) identifying relationships between and among factors of the candidate chemical reaction space.

21. A combinatorial process for selecting a best case set of factors of a chemical catalyst system, comprising;

selecting identities for factors of a candidate catalyst system for a carbonylation reaction catalysts;

defining relationships between the selected factors;

specifying a degree of factor interaction for each relationship;

generating a table of catalyzed experimental runs according to the defined relationships and specified interactions;

generating a consolidated table of candidate catalyst factors for experimental runs by combining the generated tables for the relationship; and effecting a combinatorial high throughput screening (CHTS) by reacting carbonylation reaction precursors according the experimental runs; and evaluating products of the reactions to identify a best set of catalyst factors.

22. The combinatorial process of claim 21, comprising evaluating products of the reactions by determining a turn over number from respective products of each experimental run.

23. The combinatorial process of claim 21, comprising tagging the experimental runs; determining a turn over number from respective products of each tagged experimental run; and identifying a best set of catalyst factors by relating a turn over number for each experimental run according to its tag.

24. The combinatorial process of claim 21, wherein the CHTS further comprises robotically loading an array of test wells with candidate catalyst factors according to the experimental runs and then reacting the carbonylation reaction precursors according to the experimental runs.

25. The combinatorial process of claim 21, comprising tagging the experimental runs; determining a turn over number from respective products of each tagged experimental run; and identifying a best set of catalyst factors by relating a turn over number for each experimental run according to its tag.

26. The combinatorial process of claim 21, wherein the CHTS further comprises robotically loading an array of test wells with candidate catalyst factors grouped by a common process condition according to the experimental runs and then reacting the carbonylation reaction precursors according to the experimental runs.

27. The combinatorial process of claim 21, wherein the CHTS further comprises robotically loading an array of test wells with candidate catalyst factors grouped by a common pressure, temperature or reaction time according to the experimental runs and then reacting the carbonylation reaction precursors according to the experimental runs.

28. The combinatorial process of claim 21, wherein the CHTS comprises (A) (a) reacting carbonylation reaction precursors according to the experimental runs; and (b) evaluating a set of products of said reacting step to identify best sets of catalysts and reaction conditions.

29. The combinatorial process of claim 28, further comprising (B) reiterating step (A) wherein a selected set on candidate catalysts for a step (a} of reiteration (A) is chosen as a result of an evaluating step (b) of a preceding iteration of step (A) to select a best case set of factors from said chemical experimental space.

30. The combinatorial process of claim 21, wherein the candidate catalyst factors for the experimental runs comprise a catalyst system, pressure, temperature and reaction time.

31. The combinatorial process of claim 21, wherein the candidate catalyst factors for the experimental runs comprise a catalyst system comprising a primary catalyst, metal cocatalyst and anion cocatalyst.

32. The combinatorial process of claim 21, wherein the candidate catalyst factors for the experimental runs comprise a catalyst system comprising a primary catalyst, primary catalyst amount, a metal cocatalyst, a metal cocatalyst amount, an anion cocatalyst and an anion catalyst amount.

33. The combinatorial process of claim 21, wherein the catalyst factors for the experimental runs comprise a catalyst system comprising a primary catalyst, primary catalyst amount, a metal cocatalyst, a metal cocatalyst amount, an anion cocatalyst, an anion catalyst amount, pressure, temperature, reaction time and solvent.

34. The combinatorial process of claim 21, wherein the catalyst factors for the experimental runs comprise a catalyst system comprising a primary catalyst selected from the group consisting of $Ru(acac)_3$, $Pt(acac)_2$, $Rh(acac)_3$ and $Ir(acac)_3$; a metal cocatalyst selected from the group consisting of $Mn(acac)_2$, $Fe(acac)_3$, $Co(acac)_2$ and $Ce(acac)_3$ and an anion cocatalyst comprising a hexamethylguanadinium salt.

35. The combinatorial process of claim 21, wherein the table is generated by selecting identities; defining relationships, specifying the degree of factor interaction and specifying a parameter that defines a constraint for each degree of factor relationship; and generating the table of catalyzed experimental runs according to the defined relationships, specified interactions and constraints.

36. The combinatorial process of claim 21, wherein the consolidated table is generated by a script merger process.

37. The combinatorial process of claim 21, wherein the table is generated by selecting identities; defining relationships, specifying the degree of factor interaction and specifying a parameter that defines a constraint for each degree of factor relationship; and generating the table of catalyzed experimental runs according to a deterministic procedure applied to the defined relationships, specified interactions and constraints.

38. The combinatorial process of claim 21, wherein the table is generated by selecting identities; defining relationships, specifying the degree of factor interaction and specifying a parameter that defines a constraint for each degree of factor relationship; and generating the table of catalyzed experimental runs according to a deterministic procedure applied to the defined relationships, specified interactions and constraints, wherein the deterministic procedure is selected from the group consisting of a projective plane procedure, a general product rule procedure and an exhaustive enumeration of all combinations of factor identities.

39. The combinatorial process of claim 21, wherein the table is generated by selecting identities; defining relationships, specifying the degree of factor interaction and specifying a parameter that defines a constraint for each degree of factor relationship; and generating the table of catalyzed experimental runs according to a deterministic procedure and a random algorithm applied to the defined relationships, specified interactions and constraints.

40. The combinatorial process of claim 21, wherein the table is generated by selecting identities; defining relationships, specifying the degree of factor interaction and specifying a parameter that defines a constraint for each degree of factor relationship; and generating the table of catalyzed experimental runs according to a deterministic procedure and a statistical process applied to the defined relationships, specified interactions and constraints.

41. The combinatorial process of claim 21, wherein the table is generated by selecting identities; defining relationships, specifying the degree of factor interaction and specifying a parameter that defines a constraint for each degree of factor relationship; and generating the table of catalyzed experimental runs according to a deterministic procedure and a random algorithm applied to the defined relationships, specified interactions and constraints.

* * * * *

UNITED STATES PATENT AND TRADEMARK OFFICE
CERTIFICATE OF CORRECTION

PATENT NO. : 6,728,641 B1
DATED : April 27, 2004
INVENTOR(S) : James N. Cawse

It is certified that error appears in the above-identified patent and that said Letters Patent is hereby corrected as shown below:

Column 15,
Line 65, delete "n-topple" and insert -- n-tuple --; and

Column 17,
Line 16, delete "n-topple" and insert -- n-tuple --.

Signed and Sealed this

Twenty-eighth Day of September, 2004

JON W. DUDAS
*Director of the United States Patent and Trademark Office*